(12) United States Patent
Aslam et al.

(10) Patent No.: US 9,045,413 B2
(45) Date of Patent: Jun. 2, 2015

(54) PROCESS FOR VINYL ACETATE PRODUCTION HAVING SIDECAR REACTOR FOR PREDEHYDRATING COLUMN

(71) Applicant: Celanese International Corporation, Irving, TX (US)

(72) Inventors: Naveed Aslam, Houston, TX (US); Sayanti Basu, Pasadena, TX (US); Wei Qi, Houston, TX (US)

(73) Assignee: Celanese International Corporation, Irving, TX (US)

( * ) Notice: Subject to any disclaimer, the term of this patent is extended or adjusted under 35 U.S.C. 154(b) by 112 days.

(21) Appl. No.: 14/012,176

(22) Filed: Aug. 28, 2013

(65) Prior Publication Data

US 2014/0066650 A1    Mar. 6, 2014

Related U.S. Application Data

(60) Provisional application No. 61/694,911, filed on Aug. 30, 2012.

(51) Int. Cl.
*C07C 67/05* (2006.01)
*C07C 67/055* (2006.01)

(52) U.S. Cl.
CPC .................................. *C07C 67/055* (2013.01)

(58) Field of Classification Search
CPC ........ C07C 67/055; C07C 69/15; C07C 67/05
See application file for complete search history.

(56) References Cited

U.S. PATENT DOCUMENTS

| | | |
|---|---|---|
| 3,438,870 A | 4/1969 | Roscher et al. |
| 3,838,019 A | 9/1974 | Schwerdtel et al. |
| 3,905,875 A | 9/1975 | Kronig et al. |
| 4,818,347 A | 4/1989 | Roscher et al. |
| 5,066,365 A | 11/1991 | Roscher et al. |
| 6,040,474 A | 3/2000 | Jobson et al. |
| 6,228,226 B1 | 5/2001 | Hess et al. |
| 6,476,261 B2 | 11/2002 | Ellis et al. |
| 6,696,596 B1 | 2/2004 | Herzog et al. |
| 2012/0035390 A1 | 2/2012 | Gadewar |

OTHER PUBLICATIONS

International Search Report and Written Opinion for PCT/US2013/057069 mailed Nov. 27, 2013.

*Primary Examiner* — Rosalynd Keys
*Assistant Examiner* — Jennifer C Sawyer (57) ABSTRACT

A process for producing vinyl acetate in which a secondary reactant stream is obtained from a predehydrating column and reacted in a sidecar reactor to further increase conversion of ethylene, acetic acid, and molecular oxygen and increase production of vinyl acetate.

20 Claims, 2 Drawing Sheets

PROCESS FOR VINYL ACETATE PRODUCTION HAVING SIDECAR REACTOR FOR PREDEHYDRATING COLUMN

PRIORITY CLAIM

This application claims the benefit of U.S. Provisional Application No. 61/694,911, filed on Aug. 30, 2012, the entire contents and disclosures of which is hereby incorporated by reference.

FIELD OF THE INVENTION

The present invention relates generally to processes for producing vinyl acetate that provide increased reactant conversions by utilizing a sidecar reactor with a predehydrating column.

BACKGROUND OF THE INVENTION

The preparation of vinyl acetate by reaction of ethylene with acetic acid and oxygen or oxygen-containing gases in the gas phase over fixed-bed catalysts is already known. The reaction is generally carried out at pressures from 1 to 2.5 MPa and temperatures from 100° C. to 250° C. The reaction is typically conducted in the presence of a suitable catalyst, which may comprise palladium, an alkali metal acetate promoter, and optionally a co-promoter, e.g., gold or cadmium, on a catalyst support. One exemplary vinyl acetate production process, set forth in U.S. Pat. No. 6,696,596, uses a reaction in the gas phase with oxygen or oxygen containing gasses over fixed-bed catalysts. Another example is disclosed in U.S. Pat. No. 6,040,474, which describes the manufacture of acetic acid and/or vinyl acetate using two reaction zones wherein the first reaction zone comprises ethylene and/or ethane for oxidation to acetic acid with the second reaction zone comprising acetic acid and ethylene with the product streams being subsequently separated thereby producing vinyl acetate. Also, U.S. Pat. No. 6,476,261 describes an oxidation process for the production of alkenes and carboxylic acids such as ethylene and acetic acid, which are reacted to form vinyl acetate. Each of the references mentioned above is incorporated herein by reference in its entirety.

In the multistage catalytic process, vinyl acetate and water are formed in equimolar amounts. The total oxidation of ethylene, which cannot be entirely avoided, forms carbon dioxide and water. More than 1 mol of water per mole of vinyl acetate is thus obtained. In general, the weight of water is about one quarter of the weight of the vinyl acetate formed. Apart from carbon dioxide, small amounts of other by-products, including ethyl acetate, are formed in a proportion of 1000 to 2000 wppm, based on the vinyl acetate formed. Only a small amount, e.g., not more than 250 wppm, of ethyl acetate is generally acceptable in the pure vinyl acetate. The removal of ethyl acetate requires a large amount of energy. The prior art addresses various methods of reducing the energy consumption in the purification of vinyl acetate with removal of ethyl acetate and other by-products.

The mixture used for the reaction contains a molar excess of the stoichiometrically required amount of ethylene. Accordingly, the ethylene conversion is relatively low (about 10%) and, to maintain ethylene efficiency, the unreacted ethylene has to be recirculated to the reaction zone. Product vinyl acetate is usually then separated off from the mixture of gaseous reaction products in a multistage process.

U.S. Pat. No. 4,818,347 describes a process in which the hot gas mixture leaving the vinyl acetate reactor, namely ethylene, acetic acid, vinyl acetate, water, carbon dioxide, ethyl acetate, oxygen and inerts such as, for example, nitrogen and argon, is introduced into a first distillation column which operates without additional heating, known as the pre-dewatering or predehydrating column. A gas mixture leaves the top of the predehydrating column and is brought into contact with a runback stream in a heat exchanger. The heat exchange results in the gas mixture being cooled and the runback stream being correspondingly heated. The gas mixture subsequently goes from the heat exchanger to a condenser. The material that is liquefied in the condenser is collected in a collection vessel, in which separation into an aqueous phase and an organic phase occurs. The aqueous phase may be discharged while all or part of the organic phase is recirculated as reflux to the top of the predehydrating column.

The material which has not been liquefied in the condenser may contain gaseous vinyl acetate. The gaseous vinyl acetate is scrubbed out of the gas mixture in a scrubbing column that uses acetic acid as scrubbing liquid, known as the circulating gas scrubber. The remaining tail gas is recirculated to the reactor. The bottom stream exiting the circulating gas scrubber and the remainder of the liquefied organic phase from the condensate of the predehydrating column (if any) are collected. In some cases all of the liquefied organic phase from the condensate is used as reflux to the predehydrating column and no liquefied organic phase remains.

The predehydrating column yields a bottom product comprising a mixture comprising vinyl acetate, acetic acid and about half of the water of reaction and also by-products. The other half of the water of reaction is separated without introduction of energy and forms the aqueous phase of the condensate formed on cooling of the vapor from the top of the predehydrating column, as discussed above.

The bottom product from the predehydrating column is firstly fed into a collection vessel, also referred to as the crude vinyl acetate collection vessel, and subsequently worked up in a second distillation column, known as an azeotrope column. Vinyl acetate saturated with water is obtained as overhead product. A side stream comprising ethyl acetate and a bottom product, which is recirculated to the system as recycle acetic acid, are also obtained. The side stream comprising ethyl acetate is discharged. The vinyl acetate saturated with water that is not returned as runback to the top of the second distillation column is combined with the outflow from the bottom of the circulating gas scrubber and the remainder of the liquefied organic phase from the condensate from the predehydrating column.

The mixture is subsequently fed to a third distillation column, known as the dewatering column. The vapor from the top of this column is, after condensation, virtually entirely recirculated as runback. A side offtake stream is withdrawn from the dewatering column and separated into an aqueous phase and an organic phase, with the aqueous phase then being discharged and the organic phase being returned to the column. A dry vinyl acetate/acetic acid mixture is taken off at the bottom of the dewatering column and fed to a fourth column, known as the pure vinyl acetate column. In this column, vinyl acetate, which is virtually free of ethyl acetate, is obtained as overhead product, while the bottoms from this column, which comprise acetic acid, high boilers and traces of vinyl acetate and ethyl acetate are recirculated to the process, after discharge of a substream.

Other separation systems include those described in U.S. Pat. Nos. 6,696,596; 6,476,261; 6,228,226; 6,040,474; 5,066,365; 3,905,875; 3,838,019; and 3,438,870, the entireties of which are incorporated herein by reference.

Finally, it is desirable to remove of water and ethyl acetate as early as possible in the work-up process so as to reduce the amount of these undesirable materials carried through the overall work-up process. In doing so, the associated energy-intensive removal in the pure vinyl acetate distillation column can be reduced or eliminated.

Thus, even in view of these references, the need exists for an efficient process for producing vinyl acetate.

SUMMARY OF THE INVENTION

In a first embodiment, the present invention is directed to a vinyl acetate production process comprising the steps of contacting in a primary reactor a primary reactant stream comprising acetic acid, ethylene and molecular oxygen in the presence of a first catalyst to form a primary reactor effluent comprising vinyl acetate, ethylene, oxygen, water, carbon dioxide, and acetic acid, introducing the primary reactor effluent to a predehydrating column, and obtaining a secondary reactant stream from the predehydrating column having a different composition than the primary reactor effluent, and preferably the composition of the secondary reactant stream comprises more reactants, e.g., ethylene and/or acetic acid, than the primary reactor effluent. In addition, the secondary reactant stream preferably comprises less vinyl acetate, based on weight, than the primary reactor effluent. An exemplary secondary reactor effluent preferably comprises vinyl acetate, ethylene, oxygen, water, carbon dioxide, and acetic acid. If needed additional reactants, such as ethylene, molecular oxygen, acetic acid, or combination thereof may be introduced to the secondary reactor. The process further comprises the steps of contacting in a secondary reactor the secondary reactant stream in the presence of a second catalyst to form a secondary reactor effluent, feeding the secondary reactor effluent to the predehydrating column, optionally after cooling the secondary reactor effluent, withdrawing an overhead comprising vinyl acetate from the predehydrating column, and recovering a vinyl acetate product from the overhead. The secondary reactant stream may be obtained from a vapor or liquid sidedraw from the predehydrating column.

In a second embodiment, the present invention is directed to a vinyl acetate production process comprising the steps of contacting in a primary reactor a primary reactant stream comprising acetic acid, ethylene and molecular oxygen in the presence of a first catalyst to form a primary reactor effluent comprising vinyl acetate, ethylene, oxygen, water, carbon dioxide, and acetic acid, introducing the primary reactor effluent to a predehydrating column, and withdrawing at least one stream from the predehydrating column and combining the withdrawn stream with an enriching stream comprising one of acetic acid, ethylene or molecular oxygen to form a secondary reactant stream. The process further comprises contacting in a secondary reactor the secondary reactant stream in the presence of a second catalyst to form a secondary reactor effluent that is fed to the predehydrating column, withdrawing an overhead comprising vinyl acetate from the predehydrating column, and recovering a vinyl acetate product from the overhead.

In a third embodiment, the present invention is directed to a vinyl acetate production process comprising the steps of contacting in a primary reactor a primary reactant stream comprising acetic acid, ethylene and molecular oxygen in the presence of a first catalyst to form a primary reactor effluent comprising vinyl acetate, ethylene, oxygen, water, carbon dioxide, and acetic acid and introducing the primary reactor effluent to a predehydrating column to yield an overhead and residue. The process further comprises withdrawing a vapor stream from the predehydrating column comprising ethylene, oxygen, or mixtures thereof, withdrawing a liquid stream from the residue, wherein the liquid stream comprises acetic acid, and vaporizing the vapor stream and liquid stream to form a secondary reactant stream. The process further comprises contacting in a secondary reactor the secondary reactant stream in the presence of a second catalyst to form a secondary reactor effluent that is fed to the predehydrating column, and recovering a vinyl acetate product from the overhead.

In a fourth embodiment, the present invention is directed to contacting in a primary reactor a primary reactant stream comprising acetic acid, ethylene and molecular oxygen in the presence of a first catalyst to form a primary reactor effluent comprising vinyl acetate, ethylene, oxygen, water, carbon dioxide, and acetic acid, introducing the primary reactor effluent to a predehydrating column, obtaining a secondary reactant stream from the predehydrating column having a different composition than the primary reactor effluent, contacting in a secondary reactor the secondary reactant stream in the presence of a second catalyst to form a secondary reactor effluent that is fed to the predehydrating column, withdrawing an overhead comprising vinyl acetate from the predehydrating column, condensing the overhead and separating an organic phase comprising vinyl acetate, and an aqueous phase, and recovering vinyl acetate from the organic phase. Vinyl acetate may also be recovered from the residue of the predehydrating column.

BRIEF DESCRIPTION OF DRAWINGS

The invention is described in detail below with reference to the appended drawings, wherein like numerals designate similar parts.

DETAILED DESCRIPTION OF THE INVENTION

The present invention relates to processes that incorporate a sidecar reactor with a predehydrating column to obtain higher ethylene conversions and/or acetic acid conversions. Higher conversions of either reactant may lead to improved vinyl acetate productions. By increasing the reactant conversions, the process reduces the recycle loops and provides for capital and operating efficiencies. In addition, a sidecar reactor may advantageously reduce the energy required to separate vinyl acetate.

A reactant stream is obtained, at least in part, from the predehydrating column. The secondary reatant stream has a different composition than the reactor effluent from the primary vinyl acetate reactor. In one embodiment, the reactor effluent may directly pass into the predehydrating column from the primary vinyl acetate reactor without any separation or workup. A portion of the reactant effluent is separated in the predehydrating column and may fed to a sidecar reactor that is in communication with the predehydrating column. Thus, the entire reactor effluent from the primary vinyl acetate reactor cannot pass directly into the sidecar reactor. In other words, the sidecar reactor is not in series with the primary vinyl acetate reactor. Coupling reactors in series is not expected to achieve further conversions in ethylene or acetic acid without losing vinyl acetate selectivity and/or increasing selectivity to carbon dioxide. When two reactors are in series, the vinyl acetate selectivity in the second reactor will be lower than the first reactor, because the composition of the first reactor effluent is not suitable for further reaction.

Advantageously, the predehydrating column separates a portion of the reactor effluent from the primary vinyl acetate reactor so that a reactant stream may be obtained that is suitable for converting ethylene and acetic acid into additional vinyl acetate. Preferably, the reactant stream is enriched with respect to at least one of the reactants as compared to the reactor effluent from the primary vinyl acetate reactor. In one embodiment, the reactant stream contains less vinyl acetate, based on weight, than the reactor effluent from the primary vinyl acetate reactor. Less vinyl acetate in portion of the reactor effluent reduces the possibilty of side reactions from vinyl acetate. In another embodiment, the reactant stream contains more ethylene and/or acetic acid, based on weight, than the reactor effluent from the primary vinyl acetate reactor. Preferably, the reactant stream contains more acetic acid, based on weight, than the reactor effluent from the primary vinyl acetate reactor. The additional acetic acid may promote the vinyl acetate reaction rate and improve vinyl acetate selectivity in the secondary reactor (the sidecar reactor)

In some embodiments, an enriching stream may be supplied to the sidecar reactor when the reactant stream obtained from the predehydrating column is deficient in any one of the reactants. The enriching stream may comprise acetic acid, ethylene, molecular oxygen, or mixtures thereof. The enriching stream has a different composition than the secondary reactant stream and the primary reactor effluent. In one embodiment, enriching streams may be substantially pure in the reactant, e.g., each enriching stream may comprise more than 95% of the reactant. An ethylene enriching stream may comprise at least 95% ethylene. An acetic acid enriching stream may comprise at least 95% acetic acid. An oxygen enriching stream may comprise at least 95% molecular oxygen. In one embodiments, the enriching streams may contain two reactants, e.g., 50% ethylene and 50% molecular oxygen. The enriching stream may be obtained from a separate source of reactants or from another recycle within the vinyl acetate production process. In one embodiment, the enriching stream may be obtained from a separate sidedraw of the predehydrating column or from the residue if additional acetic acid is needed.

In one embodiment, the reactant stream for the secondary reactor may be obtained by withdrawing one or more sidedraws from the predehydrating column. The sidedraw may be a vapor sidedraw that primary comprises ethylene, oxygen, or mixtures thereof, or a liquid sidedraw that comprise acetic acid and dissolved reactant gases. In some embodiments, a liquid stream may be obtained from the base of the predehydrating column or residue thereof. The liquid stream may primarily comprise acetic acid. A vaporizer may be used in some embodiments so that the sidecar reactor may operate in the vapor phase.

The sidecar reactor produces a secondary reactor effluent that is returned to the predehydrating column. Preferably, the return location for the secondary reactor effluent is above the withdrawn streams sent to the sidecar reactor. Secondary reactor effluent may be returned as a vapor stream. This allows the vinyl acetate from the sidecar reactor to be withdrawn in the overhead and not recycled through the sidecar reactor. In some embodiments, the secondary reactor effluent may be cooled, as needed, to a temperature that is similar to the reactor effluent from the primary vinyl acetate reactor. Returning a partially condensed secondary reactor effluent may keep the acetic acid in the liquid phase and vinyl acetate in the gas phase. A partially condensed secondary reactor effluent may further concentrate vinyl acetate in the top of the predehydrating column while maintaining low concentrations of acetic acid in the top. Also, cooling of the secondary reactor effluent, which is hot due to the exothermic reaction, may be necessary to control the temperature with the predehydrating column. Heat exchangers may use to capture the heat for integration with heating other streams in the process.

One advantage of the present invention is the ability to obtain improved reactant conversions. Generally the conversion of reactants is greater in the primary reactor than the conversion of the reactants in the sidecar reactors. However, the primary vinyl acetate reactor is limited in terms of conversions and cannot achieve higher conversions due to the concentration profiles, which may leads to a higher $CO_2$ selectivity with further conversions. To limit $CO_2$ selectivity, the conversion of the reactants needs to be limited. Sidecar reactors of the present invention allows the process to overcome the conversion limitations of the primary reactor without increasing the $CO_2$ selectivity. Even modest improvements in conversion, which otherwise cannot be achieved without the present invention, can lead to significant cost reductions per ton of vinyl acetate produced. In one embodiment, the overall conversion of ethylene in the primary reactor and sidecar reactor may be greater than 13%, e.g., greater than 18% or greater than 20%. In terms of ranges, the overall conversion of ethylene may be from 13% to 40%, e.g., from 18% to 30%, or from 20 to 25%. In one embodiment, the overall conversion of acetic acid in the primary reactor and sidecar reactor may be greater than 25%, e.g., greater than 35% or greater than 50%. In terms of ranges, the overall conversion of acetic acid may be from 25% to 75%, e.g., from 35% to 70%, or from 50 to 60%. In one embodiment, the overall conversion of oxygen in the primary reactor and sidecar reactor may be greater than 42.5%, e.g., greater than 50% or greater than 65%. In terms of ranges, the overall conversion of oxygen may be from 42.5% to 80%, e.g., from 50% to 75%, or from 65 to 75%.

In one embodiment, the conversion of the reactants in the sidecar reactor may be less due to the relative size of the sidecar reactor as compared with the primary vinyl acetate reactor. For example, the sidecar reactor may have a smaller height and/or diameter than the primary vinyl acetate reactor. Preferably, the sidecar reactor may be less than 5 m in height, e.g., less than 4 m in height or less than 3 m in height. Any suitable reactor may be used, such as a shell and tube reactor as described in U.S. Pat. No. 6,013,834, the entire contents and disclosures of which is hereby incorporated by reference. In an exemplary embodiment, the sidecar reactor may be a shell and tube reactor that is a similar design to the primary vinyl acetate reactor. The diameter of the shell and tube sidecar reactor may vary depending on the number of tubes. Preferably, the number of tubes in the sidecar reactor is less than the number of tubes in the primary reactor. In one embodiment, the number of tubes in the sidecar reactor may vary from 500 to 9,000, e.g., from 1,000 to 8,500 or from 1,500 to 7,000. The catalyst may be on the tube side of the reactor.

Any of the catalyst compositions known for the production of vinyl acetate, especially Group VIII metal catalysts, may be used in either the primary or sidecar reactors of the present invention. In one embodiment, it is preferred that both reactors contain a similar catalyst. Suitable catalysts for the production of vinyl acetate are described, for example, in U.S. Pat. Nos. 3,743,607; 3,775,342; 5,557,014; 5,990,344; 5,998, 659; 6,022,823; 6,057,260; and 6,472,556, all of which are incorporated herein by reference. Suitable catalysts may comprise palladium, gold, vanadium, and mixtures thereof. Particular preference is given to the catalysts palladium acetate/potassium acetate/cadmium acetate and palladium acetate/barium acetolaurate/potassium acetate. In general, the palladium content of the catalyst is from 0.5 to 5% by weight, e.g., from 0.5 to 2% by weight or from 0.6 to 1.5% by weight. When gold or one of its compounds is used, it is added in a proportion from 0.01 to 4% by weight, e.g., from 0.2 to 1.3% by weight, or from 0.3 to 1.1% by weight. The catalysts also preferably contain a refractory support, preferably a metal oxide such as silica, silica-alumina, titania or zirconia, more preferably zirconia.

The acetoxylation reaction in the primary reactor is generally carried out at pressures from 0.1 to 2.5 MPa, e.g. from 1 to 2.5 MPa or from 1 to 2 MPa, and temperatures from 50 to 200° C., e.g., from 100 to 200° C. or from 120 to 200° C. For purposes of the present invention, the acetoxylation reaction in the sidecar reactor may be carried out at similar temperature and pressure as the primary reactor. The acetoxylation reaction in the sidecar reactor is generally carried out at pressures from 0.1 to 2.5 MPa, e.g. from 1 to 2.5 MPa or from 1 to 2 MPa, and temperatures from 50 to 200° C., e.g., from 100 to 200° C. or from 120 to 200° C.

Figure 1:
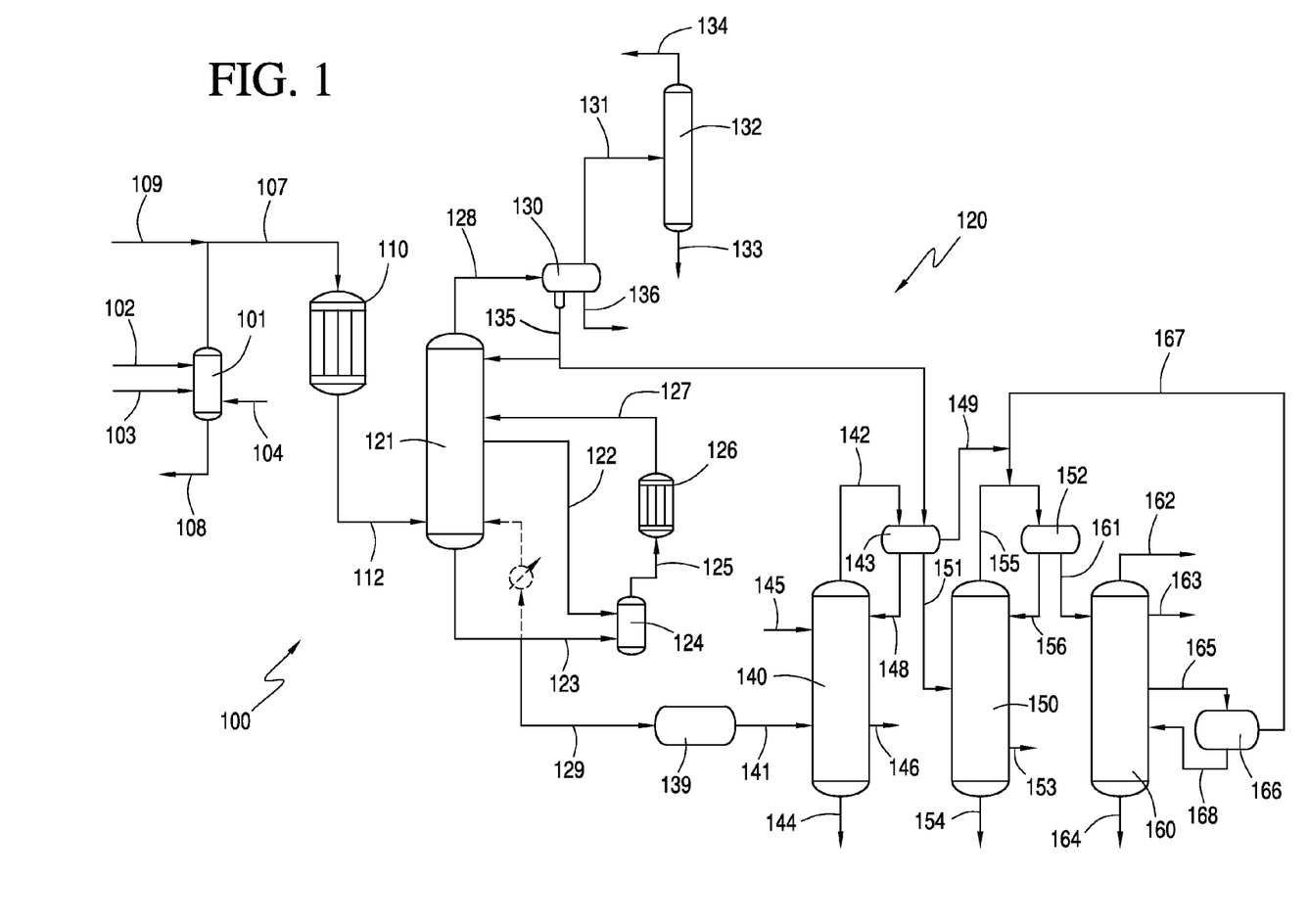
FIG. 1 is a schematic diagram of a vinyl acetate production process with sidecar reactor according to one embodiment of the present invention.

FIG. 1 illustrates an exemplary vinyl acetate synthesis system 100. Additional components and modifications may be made to the system 100 without changing the scope of the present invention. Acetic acid and ethylene are introduced to a vaporizer 101 via feed lines 102 and 103, respectively. Ethane may also be added to feed line 103. In addition, one or more recycle streams 104 may be introduced to vaporizer 101 or combined with acetic acid feed line 102. These recycle streams 104 may be withdrawn from the bottom of azeotrope column 140, dehydration column 150, and/or water stripping column 160. The temperature and pressure of vaporizer 101 may vary over a wide range. Vaporizer 101 preferably operates at a temperature from 100° C. to 250° C., e.g., from 100° C. to 200° C. or from 120° C. to 150° C. The operating pressure of vaporizer 101 preferably is from 0.1 MPa to 2.03 MPa, e.g., 0.51 MPa to 1.52 MPa. Vaporizer 101 produces a vapor feed stream 107 and a blowdown stream 108. Vapor feed stream 107 exits vaporizer 101 and combines with an oxygen source 109 prior to be fed to vinyl acetate reactor 110. In the production of vinyl acetate, the molar ratio of ethylene to oxygen is less than 6:1 in vinyl acetate reactor 110, e.g., less than 4:1 or 2.5:1. In the production of vinyl acetate, the molar ratio of acetic acid to oxygen is less than 6:1 in reactor 110, e.g., less than 3:1 or 2:1. In some embodiments, ethylene may be added to vapor feed stream 107 in a similar manner as the oxygen source 109. When ethylene is added to vapor feed stream 107 it is preferred that ethylene is not introduced to vaporizer 101.

In the production of vinyl acetate, reactor 110 produces a crude vinyl acetate stream 112 that is purified in separation system 120. Reactor 110 may be a shell and tube reactor that is capable, through a heat exchange medium, of absorbing heat generated by the exothermic reactor and controlling the temperature therein within a temperature from 110° C. to 200° C. In one embodiment, depending on conversion and reaction conditions, crude vinyl acetate stream 112 comprises from 5 to 30 wt. % vinyl acetate, from 5 to 40 wt. % acetic acid, from 0.1 to 10 wt. % water, from 10 to 50 wt. % ethylene, from 1 to 30 wt. % carbon dioxide, from 0.1 to 30 wt. % alkanes, such as methane, ethane or mixtures thereof, and from 0.1 to 15 wt. % oxygen. Optionally crude vinyl acetate stream 112 may also comprise from 0.01 to 10 wt. % ethyl acetate. Crude vinyl acetate stream 112 may comprise other compounds such as methyl acetate, acetaldehyde, acrolein, propane, and inserts such as nitrogen or argon. Generally these other compounds, except for inserts, are present in very low amounts.

Crude vinyl acetate stream 112, or a portion thereof, is fed to a lower portion of a predehydrating column 121. The energy to separate the components of crude vinyl acetate stream 112 may be provided by the heat of reaction in the primary reactor 110. In some embodiments, there may be an optional reboiler dedicated to increasing the separation energy within predehydrating column 121. Optionally, crude vinyl acetate stream 112 may be cooled to a temperature from 80° C. to 145° C., e.g., from 90° C. to 135° C., prior to being introduced into predehydrating column 121. Optionally, one or more recycle streams such as in lines 133, 136 and 135 that comprise vinyl acetate, acetic acid, water, or mixtures thereof, may be fed to predehydrating column 121 above the fed location of crude vinyl acetate stream 112.

In FIG. 1, a vapor stream 122 comprising ethylene and oxygen is withdrawn from a sidedraw of predehydrating column 121. In addition, a liquid stream 123 comprising acetic acid is withdrawn from the base of predehydrating column 121. Vapor stream 122 and liquid stream 123 are fed to a secondary vaporizer 124 to produce a secondary reactant stream 125. The operating pressure of secondary vaporizer 124 may be substantially similar to vaporizer 101, and may be from 0.1 MPa to 2.03 MPa, e.g., 0.51 MPa to 1.52 MPa. Secondary vaporizer 124 preferably operates at a temperature from 100° C. to 250° C., e.g., from 100° C. to 200° C. or from 120° C. to 180° C. Secondary reactant stream 125 is fed to sidecar reactor 126 to produce a secondary reactor effluent 127. In general, the composition of secondary reactant stream 125 is different than the primary reactor effluent, e.g., crude vinyl acetate stream 112, in terms of at least one compound. In one embodiment, at least one of the reactant compounds, e.g., ethylene, oxygen, and/or acetic acid, is in a relatively higher concentration in secondary reactant stream 125 than crude vinyl acetate stream 112. In exemplary embodiments, it is preferred to feed a stream to sidecar reactor 126 that comprises more acetic acid, based on weight, than the reactor effluent from reactor 110. Also it is preferred that less vinyl acetate is directed to sidecar reactor 126 via secondary reactant stream 125. In one optional embodiment, less carbon dioxide may be directed to sidecar reactor 126 via secondary reactant stream 125. In one embodiment, depending on conversion and reaction conditions, crude vinyl acetate stream 112 comprises from 0.1 to 20 wt. % vinyl acetate, from 5 to 40 wt. % acetic acid, from 0.1 to 15 wt. % water, from 10 to 60 wt. % ethylene, from 1 to 25 wt. % carbon dioxide, from 0.1 to 25 wt. % alkanes, such as methane, ethane or mixtures thereof, and from 0.1 to 25 wt. % oxygen. In addition, when crude vinyl acetate stream 112 comprises ethyl acetate, secondary reactant stream 125 may comprise from 0.005 to 5 wt. % ethyl acetate.

The mass flow of vapor stream 122 to liquid stream 123 may vary and may range from 1:10 to 10:1, e.g., from 1:5 to 5:1. In some embodiments, the mass flow of vapor stream 122 may be relatively larger than the mass flow of liquid stream 123.

Figure 2:
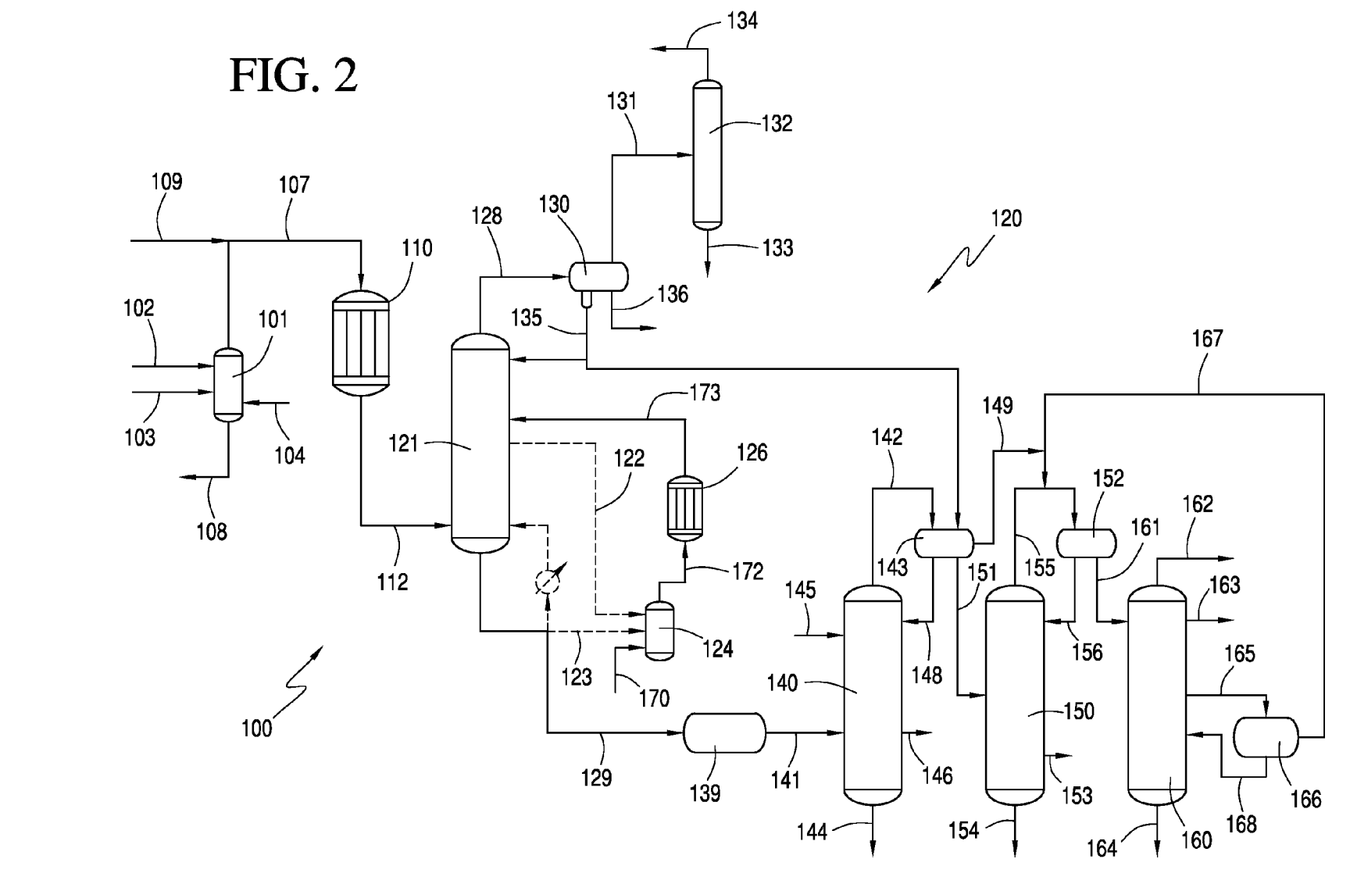
FIG. 2 is a schematic diagram of a heavy ends processing system with sidecar reactor and an enriching stream according to one embodiment of the present invention.

In FIG. 2, optionally vapor stream 122 and/or liquid stream 123 may be withdrawn from predehydrating column 121 and combined with an enriching stream 170 that comprises at least one of the reactants, namely, ethylene, acetic acid, and/or oxygen. Vapor stream 122 and/or liquid stream 123, along enriching stream 170 are fed to a secondary vaporizer 124 to produce a secondary reactant stream 172. In FIG. 2, secondary reactant stream 172 is fed to sidecar reactor 126 to produce a secondary reactor effluent 173.

In one embodiment, enriching stream 170 may be obtained from within the vinyl acetate process. For example, enriching stream 170 may comprise ethylene obtained from the vent stream 131, as discussed below.

Although one vapor stream 122 and/or liquid stream 123 is shown in FIGS. 1 and 2, it should be understood that multiple vapor and/or liquid streams may be obtained from predehydrating column 121.

As stated above, sidecar reactor 126 may operate at pressures from 0.1 to 2.5 MPa, e.g. from 1 to 2.5 MPa or from 1 to 2 MPa, and temperatures from 50 to 200° C., e.g., from 100 to 200° C. or from 120 to 200° C. A similar catalyst, comprising palladium, gold, or mixtures thereof, as used in primary reactor 110 may be used in sidecar reactor 126. Although one sidecar reactor 126 is shown in FIGS. 1 and 2, it should be understood that multiple sidecar reactors may be used in some embodiments of the present invention.

Preferably sidecar reactor 126 is a net producer of vinyl acetate. Thus, for example, in FIG. 1 secondary reactor effluent 127 may comprise more vinyl acetate, based on a relative weight percent, than secondary reactant stream 125. Also, for example, FIG. 2 secondary reactor effluent 173 may comprise more vinyl acetate, based on a relative weight percent, than secondary reactant stream 172. For purposes of the application it should be understood that when referring to secondary reactor effluent 127 the application may also be referring to secondary reactor effluent 173, unless otherwise indicated. Thus, either secondary reactor effluent is enriched in vinyl acetate with respect to at least one of the streams (vapor/liquid) obtained from predehydrating column. For example, secondary reactor effluent may comprise from 15 to 35 wt. % vinyl acetate. In addition to vinyl acetate, secondary reactor effluent may also comprise from 1 to 35 wt. % acetic acid, from 1 to 25 wt. % water, from 5 to 25 wt. % ethylene, from 0.5 to 20 wt. % carbon dioxide, from 0.1 to 15 wt. % alkanes, such as methane, ethane or mixtures thereof, and from 0.1 to 15 wt. % oxygen. Thus, secondary reactor effluent may be deficient in ethylene, oxygen, and/or acetic acid with respect to at least one of the streams (vapor/liquid) obtained from predehydrating column. This indicates that the total conversion of the reactants is improved using the sidecar reactor of the present invention. In addition, in some embodiment, sidecar reactor is operated in a manner so as to not produce a substantial amount of ethyl acetate. Thus, the amount of ethyl acetate that is fed to sidecar reactor is substantially similar to the ethyl acetate concentrations in secondary reactor effluent.

Secondary reactor effluent 127 may be cooled to a temperature from 80° C. to 160° C., e.g., from 90° C. to 135° C., prior to returning to predehydrating column 121. Secondary reactant stream 125 may be returned as a vapor, liquid stream, or a vapor-liquid stream. In one embodiment, secondary reactor effluent 127 may be returned above the locations for withdrawing the vapor and/or liquid streams from predehydrating column 121. In a vapor-liquid stream or a partially condensed secondary reactant stream 125, the acetic acid may be in the liquid phase and the vinyl acetate may be in the vapor phase. The additional heat from the exothermic reaction in sidecar reactor may further drive the separation in predehydrating column 121.

In one embodiment, predehydrating column 121 is a tray column having from 10 to 60 theoretical trays, e.g., from 15 to 55 theoretical trays. The number of actual trays for each column may vary depending on the tray efficiency, which is typically from 0.3 to 0.8 depending on the type of tray. The trays may be sieve trays, fixed valve trays, movable valve trays, or any other suitable design known in the art. In other embodiments, a packed column having structured packing or random packing may be employed.

When predehydrating column 121 is operated under 1.2 MPa, the temperature of the residue exiting in line 129 preferably is from 80° C. to 160° C., e.g., from 90° C. to 140° C. The temperature of the overhead exiting in line 128 may be from 40° C. to 125° C., e.g., from 50° C. to 110° C. As discussed above, the energy for the separation is provided form the heat of reaction in primary reactor 110 and optionally dedicated reboiler may be also used predehydrating column 121. The pressure of predehydrating column 121 may range from 0.1 MPa to 5 MPa, e.g., from 1 MPa to 2 MPa.

Predehydrating column 121 produces an overhead stream 128 and residue 129. Exemplary components of the distillate and residue compositions for predehydrating column 121 are provided in Table 1 below.

TABLE 1

| PREDEHYDRATING COLUMN | | | |
|---|---|---|---|
| | Conc. (wt. %) | Conc. (wt. %) | Conc. (wt. %) |
| Overhead | | | |
| Vinyl Acetate | 15 to 55 | 20 to 50 | 25 to 50 |
| Water | 0.1 to 10 | 0.5 to 10 | 1 to 8 |
| Ethylene | 10 to 50 | 15 to 50 | 15 to 45 |
| Oxygen | 0.1 to 10 | 0.5 to 8 | 1 to 6 |
| Carbon Dioxide | 5 to 25 | 5 to 20 | 10 to 20 |
| Methane | 0.1 to 20 | 0.5 to 15 | 1 to 10 |
| Ethane | 0.1 to 20 | 0.5 to 15 | 1 to 10 |
| Acetic Acid | 0 to 0.5 | 0 to 0.4 | 0 to 0.1 |
| Ethyl Acetate | 0 to 0.5 | 0.0001 to 0.5 | 0.001 to 0.05 |
| Residue | | | |
| Acetic Acid | 50 to 85 | 50 to 80 | 55 to 80 |
| Vinyl Acetate | 1 to 20 | 2 to 18 | 3 to 15 |
| Water | 2 to 40 | 5 to 40 | 7 to 38 |
| Ethyl Acetate | 0 to 0.5 | 0.0001 to 0.5 | 0.001 to 0.1 |

As shown in Table 1, the concentration of vinyl acetate in the residue may be reduced. This allows a reduction in the energy needed to further recover vinyl acetate from the residue. When operating without a sidecar reactor on predehydrating column, the vinyl acetate concentration may be greater than 20 wt. % in the residue. In addition, due to the higher total conversions of ethylene, acetic acid, and/or oxygen, there are relatively less of these reactants in either stream. This further assists in reducing the energy and capital requirements.

Overhead stream 128 may be cooled to a temperature of −20° C. to 50° C. and the condensate is fed to phase separator, such as decanter 130. A vent stream 131 may be scrubbed in scrubber 132 to recovery vinyl acetate in scrubbed residue 133 and produce an overhead stream 134 that is the referred to as the tailgas. Suitable scrubbing agents may include acetic acid, water, or mixtures thereof. Tailgas 134 comprises carbon monoxide, carbon dioxide, ethylene, ethane and other noncondensable gases and may be further processed to recover ethylene and oxygen for primary reactor 110. Preferably, scrubbed residue 113 may be returned to predehydrating column 121. In other embodiments, a portion of scrubbed residue 133 may be fed with residue in line 129 to further recover vinyl acetate in azeoptrope column 140.

In one embodiment, tailgas 134 that is returned to primary reactor 110 contains less volume of ethylene due to the secondary reaction in the sidecar reactor 126. This reduces the capital and operational requirements because a relatively smaller volume of ethylene is being returned to primary reactor 110. Preferably, substantially none of the unreacted ethylene from tailgas 134 is purged.

The liquid fed to decanter 130 may phase into an organic phase 135 that comprises vinyl acetate and an aqueous phase 136 that comprise water. Organic phase 135 may be refluxed, as needed, and forwarded to overhead decanter 143 of azeotrope column 140. Aqueous phase 136 may be purged or refluxed, as needed, and in some embodiments, may be fed to another column to recover vinyl acetate.

Residue 129 is directed to crude tank 139 and then fed to azeotrope column 140 via line 141. The present invention improves the operation of azeotrope column 140 by reducing the amount of vinyl acetate and/or acetic acid in residue 129, and reduces the relative size, e.g. mass flow. In some embodiments, residue 129 may bypass crude tank 139 and feed directly to azeotrope column 140. Azeotrope column 140 separates a vinyl acetate-water azeotrope from acetic acid, as well as from ethyl acetate. Acetic acid is withdrawn as the residue in line 144. Water, or a suitable azeotropic agent, is fed to column 140 via line 145 to form an azeotrope between vinyl acetate and water that is removed as distillate 142. Ethyl acetate may also be withdrawn as a sidestream 146. Distillate 142 is fed to overhead receiver 143 along with organic phase 135 from predehydrating column 121. A portion of aqueous phase 136 may also be fed to overhead receiver 143. In overhead receiver 143, the components may phase separate into a light phase and a heavy phase. The heavy phase comprises vinyl acetate and water and is fed to a dehydration column 150 via line 151. A portion of the light phase may be refluxed via line 148 to column 140. In addition, a portion of the light phase may be fed via line 149 to overhead receiver 152 of dehydration column 150.

The residue of azeotrope column 140 is withdrawn via stream 144 and may be removed or preferably returned to vaporizer 101.

Dehydration column 150 removes additional water from the contents of line 151, thus yielding purified vinyl acetate via line 153. The residue of dehydration column 150 exits via line 154 and may be recycled in part, or otherwise disposed. In other embodiments, purified vinyl acetate may be removed as the residue of the dehydration column 150. The water-containing distillate of dehydration column 150 may be directed to overhead receiver 152 via line 155. The contents of overhead receiver 152 may phase separate into an organic phase and an aqueous phase. The organic phase may be refluxed to column 150 via line 156. The aqueous phase may be directed via line 161 to water stripping column 160 to remove water.

Water stripping column 160 removes aldehydes via overhead stream 162. Overhead stream 162 comprises substantially acetaldehyde and preferably is separated as a separate byproduct for other chemical processes. Additional light ends may be removed via purge stream 163. Water is withdrawn from the bottom of column 160 via stream 164. A sidestream 165 may be withdrawn and phased in receiver 166. The organic phase in stream 167 may be fed to overhead receiver 152 of dehydration column 150. The aqueous phase in stream 168 may be fed to water stripping column 160 at a point below where sidestream 165 is withdrawn.

In one embodiment, the heating and cooling around sidecar reactor 126 may be integrated with one or more streams. For example the secondary reactant stream may be indirectly heated using a portion of the secondary reactor effluent. In addition, steam may be generated by the streams around the sidecar reactor and used through the vinyl acetate process.

In order that the invention disclosed herein may be more efficiently understood, the following Examples are provided below.

EXAMPLES

The following examples were prepared with ASPEN Plus 7.1 simulation software to test various feed composition and separation systems.

Example 1

A crude vinyl acetate stream comprising 13.7 wt. % vinyl acetate (VA), 17.7 wt. % acetic acid (HOAc), 4.5 wt. % $H_2O$, 26 wt. % ethylene ($C_2H_4$), 15.9 wt. % $CO_2$, 8.1 wt. % ethane, 7 wt. % methane and 4.6 wt. % $O_2$ was fed to a predehydrating column. The crude vinyl acetate stream has 5.5 mol % VA. Predehydrating column had 25 theoretical trays and operated at a top pressure of about 1.19 MPa and a base temperature of about 126° C. A vapor stream was withdrawn from above the feedpoint of the crude vinyl acetate stream and fed to vaporizer. Vapor stream comprised 13.7 wt. % VA, 12.6 wt. % HOAc, 5.9 wt. % $H_2O$, 27.5 wt. % $C_2H_4$, 16.9 wt. % $CO_2$, 8.6 wt. % ethane, 7.4 wt. % methane and 4.8 wt. % $O_2$. In addition, a liquid stream obtain from the base of predehydrating column was also fed to vaporizer. Liquid stream comprised 9.9 wt. % VA, 74.6 wt. % HOAc, 14.7 wt. % $H_2O$, 0.3 wt. % $C_2H_4$, and 0.3 wt. % $CO_2$. The mass flow of the vapor stream was about 98,500 lb/hr and the liquid stream had a mass flow of about 38,900 lb/hr, for a mass flow ratio of liquid stream to vapor stream of about 1:2.5.

Vapor stream and liquid stream were vaporized to produce a secondary reactant stream having a composition of 12.6 wt. % VA, 30.1 wt. % HOAc, 8.4 wt. % $H_2O$, 19.8 wt. % $C_2H_4$, 12.2 wt. % $CO_2$, 6.2 wt. % ethane, 5.3 wt. % methane and 3.5 wt. % $O_2$. The mole percent of vinyl acetate in the secondary reactant stream was 5.2%. Secondary reactant stream was fed to a sidecar reactor operating at a pressure of 1.14 MPa and temperature of 165-180° C. Sidecar reactor was a shell and tube reactor having a height of 3 m and 3000 tubes. The reaction in the sidecar reactor produced a secondary reactor effluent having a composition of 24.4 wt. % VA, 22 wt. % HOAc, 11.1 wt. % $H_2O$, 15.8 wt. % $C_2H_4$, 12.7 wt. % $CO_2$, 6.2 wt. % ethane, 5.3 wt. % methane and 0.8 wt. % $O_2$. Secondary reactor effluent was cooled to a temperature of about 126° C. and returned to predehydrating column.

The conversion for the reactants in Example 1 is shown in Table 2 below.

TABLE 2

|  | Primary Reactor | Sidecar Reactor | Total |
|---|---|---|---|
| Acetic Acid | 35.2% | 7.1% | 42.3% |
| Ethylene | 15.5% | 3% | 18.5% |
| Oxygen | 43.8% | 7.9% | 51.7% |

Using the sidecar reactor, this example was able to capture 28% more vinyl acetate in the overhead of the predehydrating column. The overhead also had 3.2% less ethylene and 13.1% less oxygen. In addition, the predehydrating has a residue with 61.8% less vinyl acetate and 6.4% less acetic acid.

Example 2

The same crude vinyl acetate stream of Example 1 was fed to a predehydrating column. Predehydrating column had 25 theoretical trays and operated at a top pressure of about 1.19

MPa and a base temperature of about 125° C. A vapor stream was withdrawn from above the feedpoint of the crude vinyl acetate stream and fed to vaporizer. Vapor stream comprised 14.4 wt. % VA, 10.5 wt. % HOAc, 6.4 wt. % $H_2O$, 27.9 wt. % $C_2H_4$, 17.1 wt. % $CO_2$, 8.7 wt. % ethane, 7.5 wt. % methane and 4.9 wt. % $O_2$. In addition, a liquid stream obtain from the base of predehydrating column was also fed to vaporizer. Liquid stream comprised 9.5 wt. % VA, 71.1 wt. % HOAc, 18.6 wt. % $H_2O$, 0.2 wt. % $C_2H_4$, and 0.3 wt. % $CO_2$. The mass flow of the vapor stream was about 260,000 lb/hr and the liquid stream had a mass flow of about 135,500 lb/hr, for a mass flow ratio of liquid stream to vapor stream of about 1:1.9.

Vapor stream and liquid stream were vaporized to produce a secondary reactant stream having a composition of 12.7 wt. % VA, 31.3 wt. % HOAc, 10.6 wt. % $H_2O$, 18.4 wt. % $C_2H_4$, 11.3 wt. % $CO_2$, 5.7 wt. % ethane, 5 wt. % methane and 3.2 wt. % $O_2$. The mole percent of vinyl acetate in the secondary reactant stream was 5.2%. Secondary reactant stream was fed to a sidecar reactor operating at a pressure of 1.14 MPa and temperature of 165-180° C. Sidecar reactor was a shell and tube reactor having a height of 4 m and 7000 tubes. The reaction in the sidecar reactor produced a secondary reactor effluent having a composition of 24 wt. % VA, 23.4 wt. % HOAc, 13.1 wt. % $H_2O$, 14.6 wt. % $C_2H_4$, 11.8 wt. % $CO_2$, 5.7 wt. % ethane, 5 wt. % methane and 0.7 wt. % $O_2$. Secondary reactor effluent was cooled to a temperature of about 124° C. and returned to predehydrating column.

The conversion for the reactants in Example 2 is shown in Table 3 below.

TABLE 3

|  | Primary Reactor | Sidecar Reactor | Total |
|---|---|---|---|
| Acetic Acid | 35.2 | 19.5 | 54.7 |
| Ethylene | 15.5 | 8.4 | 23.9 |
| Oxygen | 43.8 | 21.3 | 65.1 |

Using the sidecar reactor, this example was able to capture 45.1% more vinyl acetate in the overhead of the predehydrating column. The overhead also had 9.3% less ethylene and 37.2% less oxygen. In addition, the predehydrating has a residue with 66.1% less vinyl acetate and 17.6% less acetic acid than a predehydrating column without a sidecar reactor.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

What is claimed is:

1. A vinyl acetate production process comprising the steps of:
   contacting in a primary reactor a primary reactant stream comprising acetic acid, ethylene and molecular oxygen in the presence of a first catalyst to form a primary reactor effluent comprising vinyl acetate, ethylene, oxygen, water, carbon dioxide, and acetic acid;
   introducing the primary reactor effluent to a predehydrating column;
   obtaining a secondary reactant stream from the predehydrating column having a different composition than the primary reactor effluent;
   contacting in a secondary reactor the secondary reactant stream in the presence of a second catalyst to form a secondary reactor effluent that is fed to the predehydrating column;
   withdrawing an overhead comprising vinyl acetate from the predehydrating column; and
   recovering a vinyl acetate product from the overhead.

2. The process of claim 1, wherein the secondary reactant stream is obtained from a vapor sidedraw from the predehydrating column.

3. The process of claim 1, wherein the secondary reactant stream is obtained from a liquid stream from the predehydrating column.

4. The process of claim 1, wherein the secondary reactant stream comprises less vinyl acetate, based on weight, than the primary reactor effluent.

5. The process of claim 1, wherein the first catalyst and the second catalyst each comprise palladium, gold, or mixtures thereof.

6. The process of claim 1, wherein the secondary reactor effluent is cooled prior to be fed to the predehydrating column.

7. The process of claim 1, wherein the secondary reactor effluent comprises vinyl acetate, ethylene, oxygen, water, carbon dioxide, and acetic acid.

8. The process of claim 1, further comprising withdrawing a residue comprising vinyl acetate, acetic acid, water, and mixtures thereof from the predehydrating column and recovering vinyl acetate from the residue.

9. The process of claim 1, further comprising condensing the overhead and separating an organic phase comprising vinyl acetate, and an aqueous phase, and recovering vinyl acetate from the organic phase.

10. A vinyl acetate production process comprising the steps of:
    contacting in a primary reactor a primary reactant stream comprising acetic acid, ethylene and molecular oxygen in the presence of a first catalyst to form a primary reactor effluent comprising vinyl acetate, ethylene, oxygen, water, carbon dioxide, and acetic acid;
    introducing the primary reactor effluent to a predehydrating column;
    withdrawing at least one stream from the predehydrating column and combining the withdrawn stream with an enriching stream comprising one of acetic acid, ethylene or molecular oxygen to form a secondary reactant stream;
    contacting in a secondary reactor the secondary reactant stream in the presence of a second catalyst to form a secondary reactor effluent that is fed to the predehydrating column;
    withdrawing an overhead comprising vinyl acetate from the predehydrating column; and
    recovering a vinyl acetate product from the overhead.

11. The process of claim 10, wherein the secondary reactant stream has a different composition than the primary reactor effluent.

12. The process of claim 10, wherein secondary reactant stream is obtained from a vapor sidedraw from the predehydrating column.

13. The process of claim 10, wherein the secondary reactant stream is obtained from a liquid stream from the predehydrating column.

14. The process of claim 10, wherein the secondary reactant stream comprises less vinyl acetate, based on weight, than the primary reactor effluent.

15. The process of claim 10, wherein the first catalyst and the second catalyst each comprise palladium, gold, or mixtures thereof.

16. The process of claim 10, wherein the secondary reactor effluent is cooled prior to be fed to the predehydrating column.

17. The process of claim 10, wherein the secondary reactor effluent comprises vinyl acetate, ethylene, oxygen, water, carbon dioxide, and acetic acid.

18. The process of claim 10, further comprising withdrawing a residue comprising vinyl acetate, acetic acid, water, and mixtures thereof from the predehydrating column and recovering vinyl acetate from the residue.

19. The process of claim 10, further comprising condensing the overhead and separating an organic phase comprising vinyl acetate, and an aqueous phase, and recovering vinyl acetate from the organic phase.

20. A vinyl acetate production process comprising the steps of:
   contacting in a primary reactor a primary reactant stream comprising acetic acid, ethylene and molecular oxygen in the presence of a first catalyst to form a primary reactor effluent comprising vinyl acetate, ethylene, oxygen, water, carbon dioxide, and acetic acid;
   introducing the primary reactor effluent to a predehydrating column to yield an overhead and residue;
   withdrawing a vapor stream from the predehydrating column comprising ethylene, oxygen, or mixtures thereof;
   withdrawing a liquid stream from the residue of the predehydrating column, wherein the liquid stream comprises acetic acid;
   vaporizing the vapor stream and liquid stream to form a secondary reactant stream;
   contacting in a secondary reactor the secondary reactant stream in the presence of a second catalyst to form a secondary reactor effluent that is fed to the predehydrating column; and
   recovering a vinyl acetate product from the overhead.

* * * * *